US005259396A

United States Patent [19]

Lipari

[11] Patent Number: 5,259,396

[45] Date of Patent: Nov. 9, 1993

[54] PORTABLE, MULTI-DROP TREATMENT APPARATUS AND MULTI-DROP METHOD

[76] Inventor: Joseph J. Lipari, P.O. Box 2023, Cottonwood, Ariz. 86326

[21] Appl. No.: 844,181

[22] Filed: Mar. 2, 1992

[51] Int. Cl.[5] .......... A61G 15/00; A61F 5/00

[52] U.S. Cl. .......... 128/845; 606/242

[58] Field of Search .......... 128/845; 602/32-36, 602/39, 40; 273/280, 285; 606/242, 244, 245

[56] References Cited

U.S. PATENT DOCUMENTS

| | | | |
|---|---|---|---|
| 310,395 | 1/1885 | Farmer | 606/242 |
| 2,517,681 | 8/1950 | Koerper | 606/242 |
| 2,695,017 | 11/1954 | Herrmeyer | 606/245 |
| 3,092,102 | 6/1963 | Thompson | 606/242 |
| 3,821,953 | 7/1974 | Mikan | 606/245 |
| 3,993,051 | 11/1976 | Maruyama | 606/242 |
| 3,998,218 | 12/1976 | Lane | 606/242 |
| 4,050,454 | 9/1977 | Ekholm | 606/242 |
| 4,802,465 | 2/1989 | Slagle | 606/244 |
| 4,809,685 | 3/1989 | Barnes | 606/245 |
| 4,856,497 | 8/1989 | Westphal | 606/242 |

*Primary Examiner*—Michael A. Brown
*Attorney, Agent, or Firm*—Rosenbaum & Schwartz

[57] ABSTRACT

The present invention is a skeletal adjustment drop device which divides a single skeletal adjustment drop into a series of shorter drops that take place over a relatively longer time period to provide an equal or greater range of skeletal adjustment with reduced patient discomfort. The applied force is intermittently interrupted resulting in the application to the patient of smaller, discrete force vectors.

9 Claims, 2 Drawing Sheets

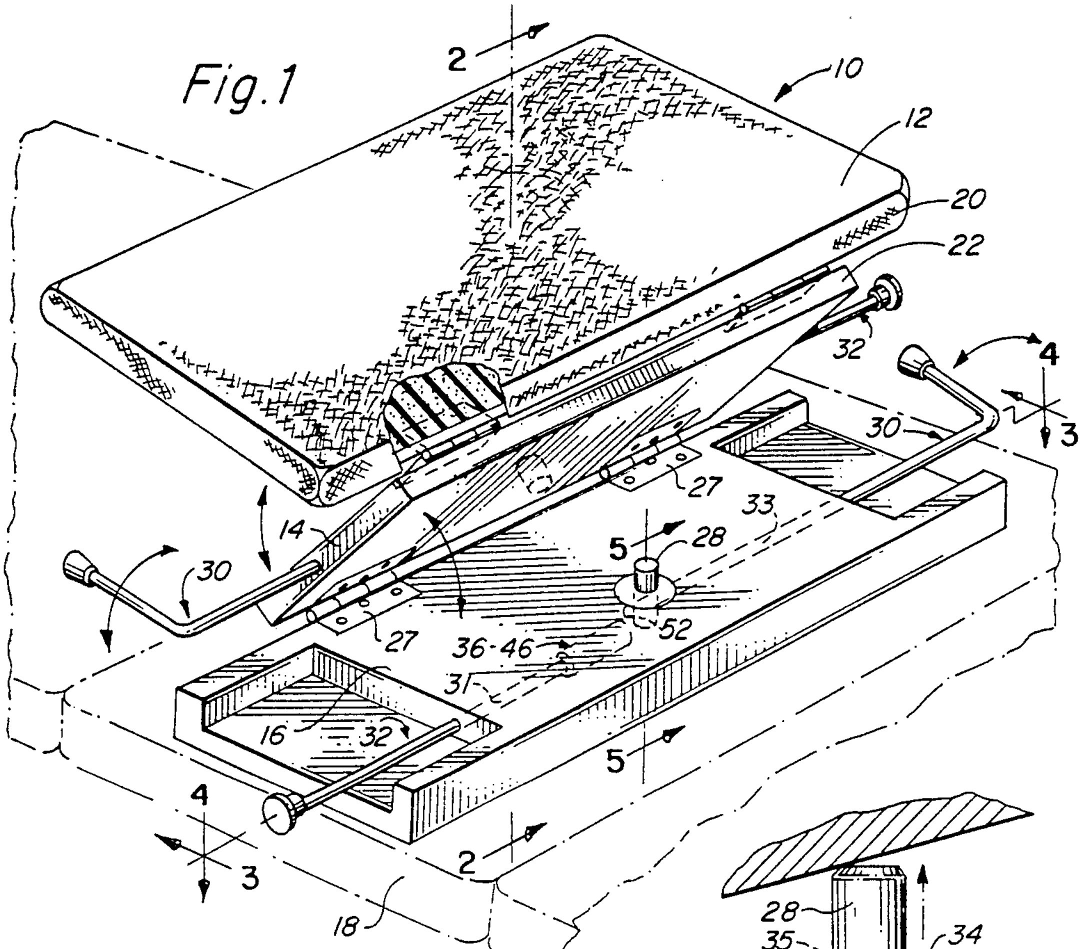
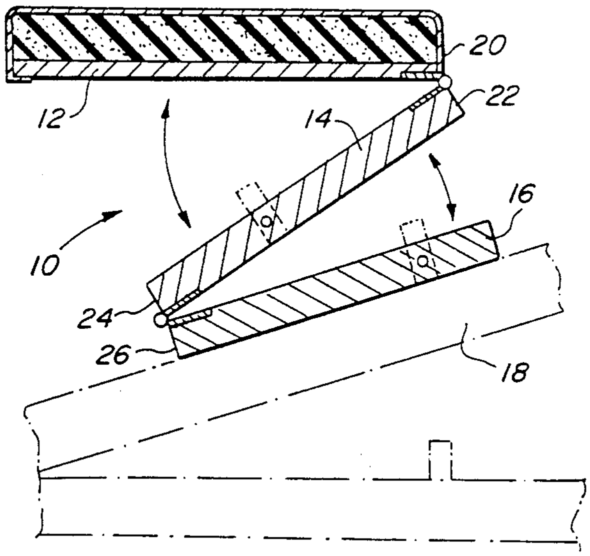
Fig. 2
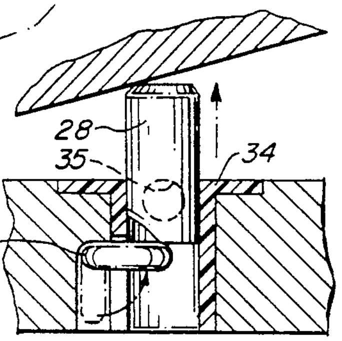
Fig.5
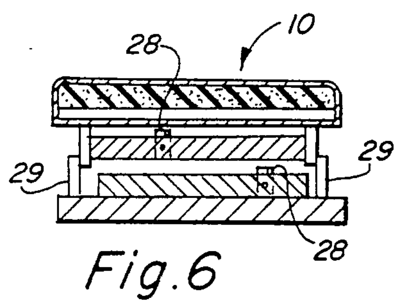
Fig.6

PORTABLE, MULTI-DROP TREATMENT APPARATUS AND MULTI-DROP METHOD

BACKGROUND OF THE INVENTION

The present invention relates generally to devices for performing human skeletal adjustment, and more particularly to a new and improved, portable, multi-drop, treatment apparatus which facilitates multiple, rapid, sequential drops to provide a greater range of skeletal adjustment with reduced patient discomfort during the adjustment process. The portable treatment apparatus is designed to enable a chiropractor or doctor to use the apparatus on both drop-equipped and non-drop equipped treatment tables.

Single drop devices are well known in the prior art and are designed to adjust the patient's skeletal area in need of adjustment in one continuous motion. The patient experiences the total force of the single drop apparatus all at once. This causes a relatively major, rapid, skeletal adjustment often resulting in severe patient discomfort. Many examples of such drop tables or drop devices exist in the pertinent prior art.

U.S. Pat. No. 4,856,497 by Westphal discloses a portable, collapsible, treatment table with drop sections. This patent discloses a base member having a lifting handle which is in engagement with a piston or lift column mounted in a vertical bore in the base member. The piston or lift column is provided with an annular groove which engages a ball-bearing. The amount of pressure exerted on the ball-bearing in the detent is governed by a threaded adjustment shaft which laterally extends into the base member perpendicular to the vertical piston bore. Adjustment of the screw exerts varying degrees of pressure on the ball-bearing and thereby on the detent of the piston.

When the assembly is cocked by engaging the lift handle, the lift column moves upwardly until the ball-bearing is seated in the lower annular groove. The amount of pressure exerted by the ball-bearing in the groove determines the amount of drop pressure that must be applied on the elevated cushion to move the cushion rapidly downward for a drop action, thereby making the needed chiropractic adjustments on the patients. It is known, therefore, that by tightening or loosening the tension control knob, the desired amount of applied pressure can be controlled for the drop mechanisms. Each of the drop mechanisms on this table are similarly constructed, and there are drops provided for the neck, back, and pelvic regions of the patient. While this patent discloses a structure which is analogous to that of the present invention, this patent clearly does not show the combination of multiple drop mechanisms used in series to break discrete skeletal adjustments into smaller sequential drops as contemplated by the present invention.

SUMMARY OF THE INVENTION

The present invention comprises a new and improved, portable, skeletal adjustment apparatus which has a multiplicity of drop mechanisms that can be used in conjunction with single-drop or non-drop chiropractic tables or surfaces. An object of the invention is to lessen patient discomfort by distributing the total applied force of the adjustment drop over a series of discrete drops. The apparatus allows the practitioner an equal or greater range of skeletal adjustments than are available with devices in the prior art, and permits larger overall drops due to its multiple drop configuration.

The multiple drop apparatus sub-divides an individual adjustment drop into a series of smaller, discrete drop components which distribute and diffuse the force applied to the patient's body over both a relatively longer time period and shorter incremental drop distances than do the conventional drop devices. The apparatus also permits larger overall drops due to its multiple drop configuration. Adjustments are provided in conjunction with each individual drop mechanism to vary the amount of applied force necessary to trigger each mechanism.

These and other objects, features, and advantages of the present invention will become more apparent to those skilled in the art from the following detailed description of the invention, which references the accompanying drawings.

BRIEF DESCRIPTION OF THE DRAWINGS

FIG. 1 is a perspective elevational view of the present invention with the planar members shown unfolded.

FIG. 2 is a cross-sectional view taken along line 2—2 of FIG. 1 showing the present invention being used in conjunction with a standard one-drop table shown in phantom.

FIG. 5 is an elevational view of an exposed lift piston assembly separating two planar members.

FIG. 6 is an embodiment of the invention showing an alternative means of operatively coupling the planar members.

DETAILED DESCRIPTION OF THE PREFERRED EMBODIMENT

Figures 3, 4:
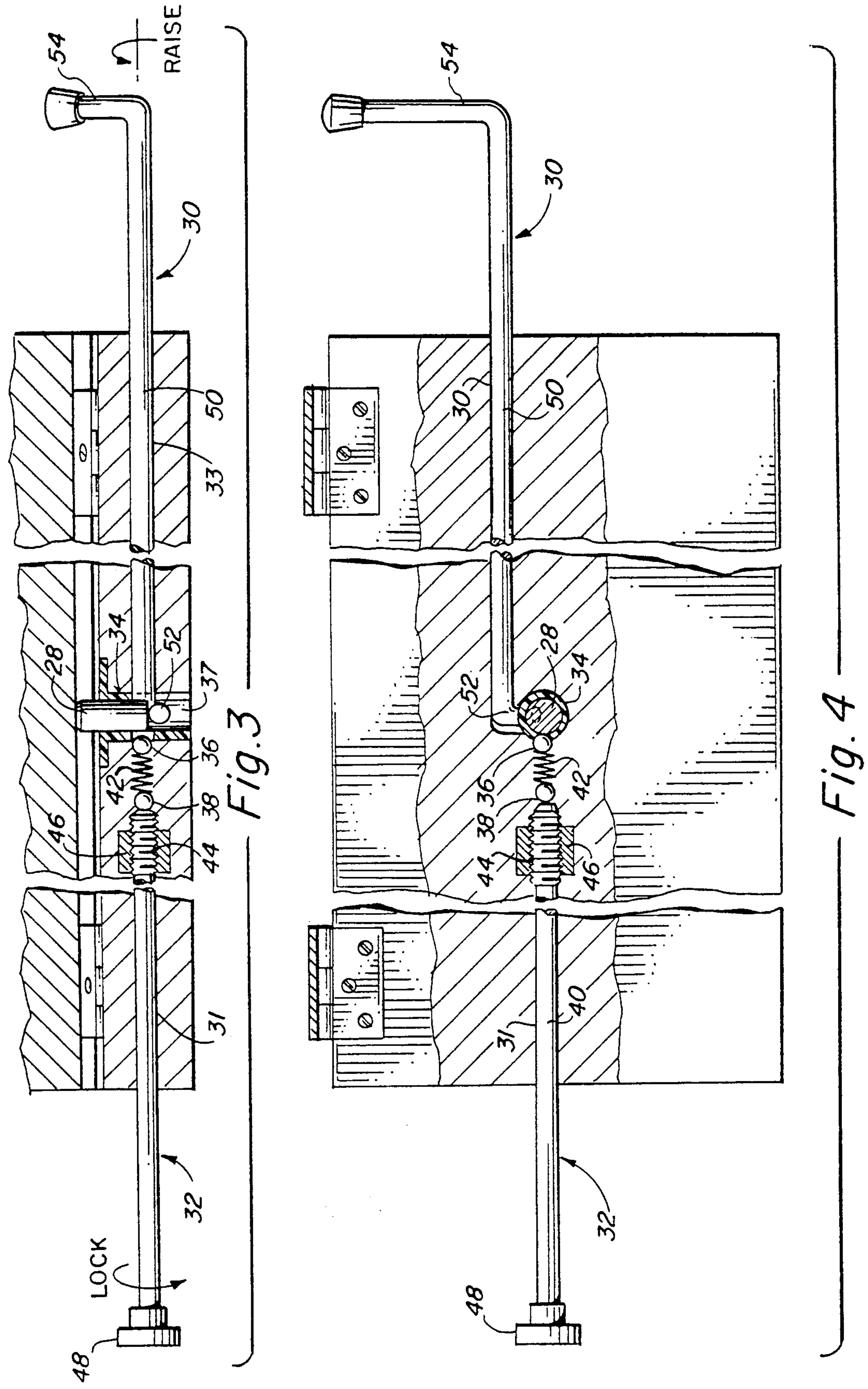
FIG. 3 is an elevational view of an exposed lift and drop mechanism in use with the piston in the up position thereby separating two planar members.
FIG. 4 is a cross-sectional view taken along line 4—4 of FIG. 1.

With reference to FIGS. 1 and 2, there is shown one embodiment of the present invention 10, which consists generally of at least three planar members; a top planar member 12, a middle planar member 14, and a base planar member 16. Planar members 12, 14, and 16 are composed of material of sufficient strength to withstand the weight of the patient and the forces applied to the device 10 during use. Base planar member 16 rests on and is parallel to an underlying support surface 18. Underlying support surface 18 may be a non-drop treatment table or a single-drop treatment table such as that shown by Westphal U.S. Pat. No. 4,856,497. The upwardly facing side of top planar member 12 may be padded for patient comfort, and the downwardly facing side of base planar member 16 may be of increased area for stability and support.

Top planar member 12 is operatively coupled to intermediate planar member 14 along their edges 20 and 22. Intermediate planar member 14 is, in turn, operatively coupled to planar member 16 along their edges 24 and 26. The operative couples may be any hinged components, such as hinges 27, of sufficient strength to withstand the weight of the planar members and the forces exerted on them during use, or may be linear tracks 29, as shown in FIG. 6, of sufficient strength to withstand reciprocal slidable motion of the various planar members with respect to each other.

Installed within both planar members 14 and 16 are the internal operational components which permit the drop functioning of the device. The operational components consist of a movable piston 28 which, when set, projects outwardly from a top surface of each of the planar members 14 and 16, and is substantially centrally located on that surface; a setting mechanism 30, more fully described below, which is operably associated with piston 28 to set piston 28 to the activation or "up" position; and a tensioning means 32, more fully described below, to create resist in piston 28 during activation of the drop mechanism to vary the amount of applied pressure necessary to release the set piston 28.

Now referring to FIGS. 3 and 4, the internal operational components of planar members 14 and 16 are installed in opposing bores 31 and 33 in the planar members. In particular, a piston seat 34, as shown in FIG. 5, is fixably inserted into a bore drilled in a perpendicular orientation to the plane of and through each of planar members 14 and 16 at a location substantially in their centers. Piston 28 rides in an up and down fashion within piston seat 34. Lateral bores 31 and 33 in planar members 14 and 16 are positioned such that they interconnect with the passageway created for insertion of piston seat 34. Each of bores 31 and 33 are substantially centrally located with respect to the thickness of planar members 14 and 16, and also substantially centrally located along the longitudinal axis of the two planar members 14 and 16.

Tensioning means bore 31 is located such that its center line interconnects the longitudinal center line that passes through the center of piston 28. Tensioning means bore 31 contains tensioning means 32 for creating in piston 28 resistance to force that is applied to the device 10 during use. Tensioning means 32 includes a ball-bearing 36, which rides in tensioning means bore 31 and comes in contact with a seat 35 on the side of piston 28, another ball-bearing 38 which rides in bore 31 between first ball-bearing 36 and tensioning rod 40, and spring 42 which rests between and separates the two ball-bearings 36 and 38. Pressure is applied to second ball-bearing 38 through tension rod 40 by turning it in a clockwise manner. The inner end of tension rod 40 is threaded and threads 44 of tension rod 40 ride in threaded insert 46 that is fixably seated within planar members 14 and 16 along the longitudinal axis of tensioning means bore 31. Tension rod 40 has twist handle 48 on its outer end for adjustment purposes.

The longitudinal axis of setting mechanism bore 33 is located slightly off center to the longitudinal center line that runs through the center of piston 28. Setting mechanism bore 33 contains setting mechanism 30 for setting piston 28 in the up position when preparing to use or actuate the device 10. Setting mechanism 30 consists of a setting rod 50, whose inner end 52 has an "L" configuration. Inner end 52 rides within the piston seat cavity 37 such that when setting rod 50 is turned clock-wise inner end 52 comes in contact with the bottom of piston 28, pushes piston 28 up, and sets it in the up position. The outer end 54 of setting rod 50 also has an "L" configuration which comprises a handle for turning in a clock-wise direction to set piston 28 in the up position. Setting mechanism 30 may also include an associated actuator 39 which actuates setting mechanism 30 to raise piston 28 within cavity 37. Actuator 39 may be any of an electromechanical, pneumatic or hydraulic actuating device, which is capable of rotational movement for actuating the setting mechanism 30. Such actuators are well known in the art. Setting mechanism 30 is used to set the device 10 immediately prior to use or actuation, and tensioning means 32 is used to prescribe the amount of force that the practitioner must apply to the patient's body to activate the drop mechanism. Setting mechanism 30 and tensioning means 32 of planar members 14 and 16 are positioned on opposite sides of the device 10 from each other to facilitate ease of adjustment.

As shown in FIG. 2, the present invention 10 may be used in conjunction with a standard single-drop table or device, shown in phantom, to increase the number of drops available for use by the practitioner.

To use the device 10, the practitioner would first set the piston 28 in the up position using setting mechanism 30, and then apply tension to piston 28 with tensioning means 32. The amount of tension applied depends on the area of the patient's body to be adjusted and the weight of the patient. If the body area in need of adjustment is, for example, the patient's neck area, a relatively lesser degree of tension would be set, the device 10 would be placed on the practitioner's non-drop or single-drop table, and the patient would then be placed on the table with his head and neck area on the device 10. The practitioner would then be able to complete the adjustment process by applying enough pressure to the patient's head and neck area to trigger the drop mechanisms of the device 10.

While the present invention has been described above with reference to the preferred embodiment, those skilled in the art will understand and appreciate that variations may be made, including but not limited to variations in design, detail, size, shape, and choice of materials for manufacture, with the resulting device still falling within the spirit and scope of the present invention which is intended to be limited only by the following claims.

What is claimed is:

1. A method for human skeletal adjustment comprising the steps of:

(a) setting a plurality of releasable vertically interdisposed planar members such that said planar members are raised above one another;

(b) positioning a patient's bodily area in need of adjustment on a top planar member of said plurality of releasable vertically interdisposed planar members; and (c) applying pressure to said bodily area in need of skeletal adjustment to trigger the release of said vertically interdisposed planar members.

2. An apparatus for human skeletal adjustment which comprises:

(a) a top planar member for supporting a patient's bodily area in need of skeletal adjustment;

(b) a base planar member;

(c) at least one intermediate planar member vertically interdisposed between said top and said base planar members and operatively coupled therebetween; and (d) means for releasable elevation of said top planar member and said at least one intermediate member, operably installed in each of said base planar member and said at least one intermediate planar member.

3. The apparatus of claim 2, wherein said at least one intermediate planar member comprises a plurality of releasable planar members in vertical alignment with one another.

4. The apparatus in claim 3, wherein said means for releasable elevation of said top and at least one intermediate planar members is comprised of a releasable support element, raiseable through setting means, to raise and support each of said top and said at least one intermediate planar members above a top surface of their adjacent lower planar members respectively, and adjustable tensioning means to prescribe an amount of pressure necessary to apply to said device so as to trigger said releasable support element.

5. An apparatus for human skeletal adjustment which comprises:

(a) a top planar member for supporting a patient's bodily area in need of skeletal adjustment with the top surface of said top planar member being cushioned for patient comfort;

(b) a base planar member;

(c) at least one intermediate planar member vertically interdisposed between said top and said base planar members and hingedly connected to said top and said base planar members at opposite sides of said at least one intermediate planar member; and (d) lift and drop means for releasable elevation of said top planar member and said at least one intermediate planar member, operably installed in each of said base planar member and said at least one intermediate planar member.

6. The apparatus of claim 5, wherein said at least one intermediate planar member comprises a plurality of releasable planar members in vertical alignment with one another.

7. The apparatus of claim 6, wherein said lift and drop means for releasable elevation of said top and at least one intermediate planar members in comprised of a releasable piston, raiseable through setting means, to raise and support each of said top and said at least one intermediate planar members above a top surface of their adjacent lower planar members respectively, and adjustable tensioning means to exert a lateral force on said releasable piston thereby prescribing an amount of pressure necessary to apply said device so as to trigger said releasable piston.

8. The apparatus of claim 7, wherein said setting means is comprised of a setting rod that engages said releasable piston within at least one of said base planar member or said at least one intermediate planar member, and is accessible for setting purposes through a setting handle external to at least one of said base planar member or said at least one intermediate planar member.

9. The apparatus of claim 7, wherein aid adjustable tensioning means is comprised of a tensioning rod that forcibly engages said releasable piston within at least one of said base planar member or said at least one intermediate planar member and is accessible for tensioning purposes through a tensioning handle external to at least on of said base planar member or said at least one intermediate planar member.

* * * * *